(12) United States Patent
Chanduszko et al.

(10) Patent No.: US 7,806,846 B2
(45) Date of Patent: Oct. 5, 2010

(54) RESTORATION OF FLOW IN LAA VIA TUBULAR CONDUIT

(75) Inventors: Andrzej J. Chanduszko, Chandler, AZ (US); Paul A. Garant, Nashua, NH (US)

(73) Assignee: NMT MEdical, Inc., Boston, MA (US)

( * ) Notice: Subject to any disclaimer, the term of this patent is extended or adjusted under 35 U.S.C. 154(b) by 350 days.

(21) Appl. No.: 11/092,130

(22) Filed: Mar. 29, 2005

(65) Prior Publication Data

US 2005/0222533 A1 Oct. 6, 2005

Related U.S. Application Data

(60) Provisional application No. 60/557,485, filed on Mar. 30, 2004.

(51) Int. Cl.
*A61M 5/00* (2006.01)
(52) U.S. Cl. .......................................................... 604/8
(58) Field of Classification Search ............... 604/8–10; 606/185, 213
See application file for complete search history.

(56) References Cited

U.S. PATENT DOCUMENTS

| | | | |
|---|---|---|---|
| 5,192,301 A | | 3/1993 | Kamiya et al. |
| 5,306,234 A | | 4/1994 | Johnson |
| 5,382,261 A | | 1/1995 | Palmaz |
| 5,456,693 A | | 10/1995 | Conston et al. |
| 5,823,198 A | | 10/1998 | Jones et al. |
| 5,865,791 A | | 2/1999 | Whayne et al. |
| 5,893,869 A | * | 4/1999 | Barnhart et al. ............ 606/200 |
| 5,984,917 A | | 11/1999 | Fleischman et al. |
| 6,007,558 A | | 12/1999 | Ravenscroft et al. |
| 6,096,347 A | | 8/2000 | Geddes et al. |
| 6,152,144 A | * | 11/2000 | Lesh et al. ................. 128/898 |
| 6,231,561 B1 | * | 5/2001 | Frazier et al. .............. 604/500 |
| 6,290,674 B1 | | 9/2001 | Roue et al. |
| 6,328,727 B1 | * | 12/2001 | Frazier et al. .............. 604/500 |
| 6,408,981 B1 | | 6/2002 | Smith et al. |
| 6,419,669 B1 | | 7/2002 | Frazier et al. |
| 6,423,051 B1 | | 7/2002 | Kaplan et al. |
| 6,436,088 B2 | | 8/2002 | Frazier et al. |
| 6,447,539 B1 | | 9/2002 | Nelson et al. |

(Continued)

FOREIGN PATENT DOCUMENTS

WO        WO 99/05977        2/1999

(Continued)

OTHER PUBLICATIONS

Moene, R.J. et al, "Anastomosis between the Atrial appendages in a Patient with Juxtaposition", Chest, vol. 59, pp. 583-586, 1971.*

(Continued)

*Primary Examiner*—Melanie J Hand
(74) *Attorney, Agent, or Firm*—Helen S. Liu

(57) ABSTRACT

An opening other than the ostium of a left atrial appendage (LAA) is provided to allow blood flow between the LAA and another portion of the body. The opening has a conduit that helps to increase blood flow through an LAA by adding at least one other flow path to the ostium, thereby reducing the risk of stasis and the formation of thrombi.

19 Claims, 2 Drawing Sheets

U.S. PATENT DOCUMENTS

| | | | |
|---|---|---|---|
| 6,458,100 B2 | 10/2002 | Roue et al. | |
| 6,485,407 B2 | 11/2002 | Alferness et al. | |
| 6,488,689 B1 | 12/2002 | Kaplan et al. | |
| 6,551,303 B1 | 4/2003 | Van Tassel et al. | |
| 6,561,969 B2 | 5/2003 | Frazier et al. | |
| 6,641,557 B1 | 11/2003 | Frazier et al. | |
| 6,652,555 B1 | 11/2003 | Van Tassel et al. | |
| 6,652,556 B1 | 11/2003 | Van Tassel et al. | |
| 6,666,861 B1 | 12/2003 | Grabek | |
| 6,689,150 B1 | 2/2004 | Van Tassel et al. | |
| 6,712,804 B2 | 3/2004 | Roue et al. | |
| 6,712,836 B1 | 3/2004 | Berg et al. | |
| 7,128,073 B1 | 10/2006 | van der Burg et al. | |
| 7,152,605 B2 | 12/2006 | Khairkhahan et al. | |
| 2001/0025132 A1 | 9/2001 | Alferness et al. | |
| 2001/0034537 A1 | 10/2001 | Shaw et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0049492 A1 | 12/2001 | Frazier et al. | |
| 2002/0016626 A1 | 2/2002 | DiMatteo et al. | |
| 2002/0022860 A1 | 2/2002 | Borillo et al. | |
| 2002/0035374 A1 | 3/2002 | Borillo et al. | |
| 2002/0049457 A1 | 4/2002 | Kaplan et al. | |
| 2002/0099390 A1 | 7/2002 | Kaplan et al. | |
| 2002/0103492 A1 | 8/2002 | Kaplan et al. | |
| 2002/0111637 A1 | 8/2002 | Kaplan et al. | |
| 2002/0111647 A1 | 8/2002 | Khairkhahan et al. | |
| 2002/0183823 A1 | 12/2002 | Pappu | |
| 2003/0023262 A1 | 1/2003 | Welch | |
| 2003/0023266 A1 | 1/2003 | Borillo et al. | |
| 2003/0057156 A1 | 3/2003 | Peterson et al. | |
| 2003/0073979 A1 | 4/2003 | Naimark et al. | |
| 2003/0083542 A1 | 5/2003 | Alferness et al. | |
| 2003/0100920 A1* | 5/2003 | Akin et al. | 606/213 |
| 2003/0120337 A1 | 6/2003 | Van Tassel et al. | |
| 2003/0181942 A1 | 9/2003 | Sutton et al. | |
| 2003/0191526 A1 | 10/2003 | Van Tassel et al. | |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0030335 A1 | 2/2004 | Zenati et al. | |
| 2004/0034366 A1 | 2/2004 | van der Burg et al. | |
| 2004/0044361 A1 | 3/2004 | Frazier et al. | |
| 2004/0049210 A1 | 3/2004 | Van Tassel et al. | |
| 2004/0064138 A1 | 4/2004 | Grabek | |
| 2004/0073241 A1 | 4/2004 | Barry et al. | |
| 2005/0043759 A1* | 2/2005 | Chanduszko | 606/213 |
| 2005/0070952 A1 | 3/2005 | Devellian | |
| 2005/0101984 A1* | 5/2005 | Chanduszko et al. | 606/185 |
| 2005/0222533 A1 | 10/2005 | Chanduszko et al. | |
| 2005/0234540 A1 | 10/2005 | Peavey et al. | |
| 2005/0234543 A1 | 10/2005 | Glaser et al. | |

FOREIGN PATENT DOCUMENTS

| | | |
|---|---|---|
| WO | WO 99/30640 | 6/1999 |
| WO | WO 01/21247 | 3/2001 |
| WO | WO 01/30266 | 5/2001 |
| WO | WO 01/30267 | 5/2001 |
| WO | WO 01/30268 | 5/2001 |
| WO | WO 01/78596 | 10/2001 |
| WO | WO 02/17809 | 3/2002 |
| WO | WO 03/063732 | 8/2003 |

OTHER PUBLICATIONS

Lindsay, B., "Obliteration of the Left Atrial Appendage: A Concept worth testing," Society of Thoracic Surgeons, 1996.

Blackshear, et al., "Appendage Obliteration to Reduce Stroke in Cardiac Surgical Patents with Atrial Fibrillation," Society of Thoracic Surgeons, 1996.

Oneglia. et al., "Left Atrial Appendage Thrombus as a source of peripheral embolism," Echocardiography: Jrnl of CV ultrasound & Allied Tech., 2001.

Al-Saady, et al., "Left atrial appendage: structure, function, and role in thromboembolism," Heart, 1999.

Nakai, et al., Percutaneous Left Atrial Appendage Occlusion (PLAATO) for preventing Cardioembolism, Circulation, 2002.

Stollberger, et al., "Is percutaneous left atrial appendage transcatheter occlusion an alternative to oral anticoagulation in patients with atrial fibrillation?" letter to the editor.

Meier, et al., "Contemporary management of patent foramen ovale," Circulation, 2003.

Disesa, et al, "Ligation of the left atrial appendage using an automatic surgical stapler," Society of Thoracic Surgeons, 1988.

Crystal, et al, "Left atrial appendage occlusion study (LAAOS): a randomized clinical trial of left atrial appendage occlusion during routine coronary artery bypass graft surgery for long-term stroke prevention." American Heart Journal, 2003.

Lynch, et al., "Recanalization of the left atrial appendage demonstrated by transesophageal echocardiography," Society of Thoracis Surgeons, 1997.

Odell, et al., "Thoracoscopic Obliteration of the left atrial appendage: Potential for stroke reduction?" Society of Thoracis Surgeons, 1996.

Sievert, et al., "Percutaneous Left Atrial Appendage Transcatheter occlusion to prevent stroke in high-risk patients with atrial fibrillation," Circulation, 2002.

Omran, et al., "Mechanical Occlusion of the left atrial appendage," University of Bonn.

Nakai, et al., "An endovascular approach to cardioembolic stroke prevention in atrial fibrillation patents," PACE, 2003.

Shirani, et al., "Structural remodeling of the left atrial appendage in patients with chronic non-valvular atrial fibrillation: implications for thrombus formation, systemic embolism, and assessment by transesophageal echocardiography," Cardiovascular Pathology, 2000.

Aeba, et al, "Left atrial appendage insertion for right ventricular outflow tract reconstruction," Society of Thoracis Surgeons, 2001.

Kimura, et al., "Effect of Low-Intensity Warfarin Therapy on Lett Atrial Thrombus Resolution in Patients with Nonvalvular Atrial Fibrillation," Japanese Circulation Journal, Apr., 2001.

* cited by examiner

RESTORATION OF FLOW IN LAA VIA TUBULAR CONDUIT

CROSS-REFERENCE TO RELATED APPLICATION

This application claim priority from provisional application Ser. No. 60/557,485, filed Mar. 30, 2004, which is incorporated herein by reference.

BACKGROUND OF THE INVENTION

Arrhythmias are abnormal heart rhythms that may cause the heart to function less effectively. Atrial fibrillation (AF) is the most common abnormal heart rhythm. In AF, the two upper chambers of the heart (i.e., the atria) quiver rather than beat and, consequently, fail to entirely empty of blood. As blood stagnates on the walls of the atria, it may form thrombi (i.e., clots). Under certain circumstances, these thrombi can re-enter circulation and travel to the brain, causing a stroke or a transient ischemic attack (TIA).

Research has indicated that as many as ninety (90) percent of all thrombi formed during AF originate in the left atrial appendage (LAA). The LAA 11 is a remnant of an original embryonic left atrium that develops during the third week of gestation. As shown in FIG. 1, it is located high on the free wall of the left atrium 12. Long, tubular, and hook-like in structure, the LAA 11 is connected to the left atrium 12 by a narrow junction 14, referred to as the "ostium" (FIG. 1). The precise physiological function of the LAA remains uncertain. Recent reports suggest it may maintain and regulate pressure and volume in the left atrium; modulate the hemodynamic response during states of cardiac stress; mediate thirst in hypovolemia; and/or serve as the site of release of both the peptide hormone atrial natriuretic factor (ANF), which stimulates excretion of sodium and water by the kidneys and regulates blood pressure, and stretch sensitive receptors, which regulate heart rate, diuresis, and natriuresis.

The high rate of thrombus formation in the LAA is believed to be attributable to its physical characteristics. Blood easily stagnates and thereafter can clot in the long, tubular body of the LAA or at its narrow ostium. In contrast, a right atrial appendage (RAA), which is a wide, triangular appendage connected to the right atrium by a broad ostium, is infrequently the site of thrombus formation. Thrombus formation in the LAA is further promoted by the numerous tissue folds 13 (i.e., crenellations) on its interior surface (FIG. 1). These crenellations 13 are particularly hospitable to blood stagnation and clotting, especially when the heart is not functioning at maximum capacity. Thrombi formed in the LAA can re-enter the circulation upon conversion of AF to normal rhythm (i.e., cardioversion).

Certain patient subsets are considered to be at an abnormally high risk of thrombus formation. Such patients include those over seventy-five (75) years of age, as well as those presenting with a history of thromboembolism, significant heart diseases, decreased LAA flow velocity, increased LAA size, spontaneous echogenic contrast, abnormal coagulation, diabetes mellitus, and/or systemic hypertension. For these high-risk patients, prophylactic intervention may be recommended. Currently proposed prophylaxes generally fall into three categories: (1) surgical ligation of the LAA; (2) implantation of an LAA occluder sufficient to prevent, or at least minimize, blood flow into the LAA; and (3) placement of a filter in the LAA ostium to prevent clots formed therein from re-entering the circulatory system.

Because of the uncertain physiological role of the LAA, its obliteration and occlusion are controversial. Reports have suggested that obliteration of the LAA may decrease atrial compliance and diminish ANF secretion. Furthermore, while properly positioned filter devices prevent migration of thrombi into the circulatory system, they cannot inhibit thrombus formation within the LAA. Consequently, in the event the filter device is dislodged or ineffectively sealed against the LAA ostium, clots held at the LAA ostium by the filter could be released into the circulation.

SUMMARY OF THE INVENTION

In embodiments of the present invention, the left atrial appendage (LAA) is attached to the left atrium at an ostium, and apparatus and methods are provided for allowing blood flow from the LAA to another portion of the body through an opening other than the ostium. The opening preferably has a conduit, and is preferably to the main body of the left atrium. The conduit helps to increase blood flow through an LAA by adding at least one other flow path to the ostium, and thereby reduces the risk of stasis and the formation of thrombi.

A conduit could be any suitable size, but is preferably small enough or compressible enough to be provided through a catheter of no more than about 12 French (F), and preferably less than 5 F. Materials that could be used include any biocompatible metal or polymer, including nitinol; if a polymer is used, it can be desirable to make the conduit radiopaque.

Unlike other methods that focus on closing, occluding or reducing the volume of the LAA using plugs, membranes, or sutures, these embodiments promote constant flow through the appendage in the event of AF. These methods do not require obliteration of the LAA and the functions it serves. Other features and advantages will become apparent from the following detailed description and drawings.

DETAILED DESCRIPTION

Figure 1:
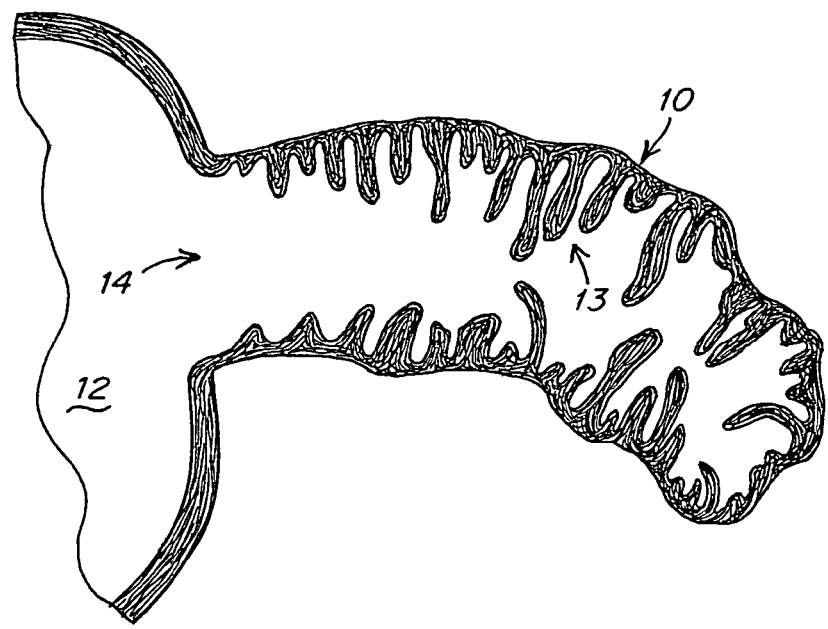
FIG. 1 is a prior art cross-sectional general view of an LAA.
Figure 2:
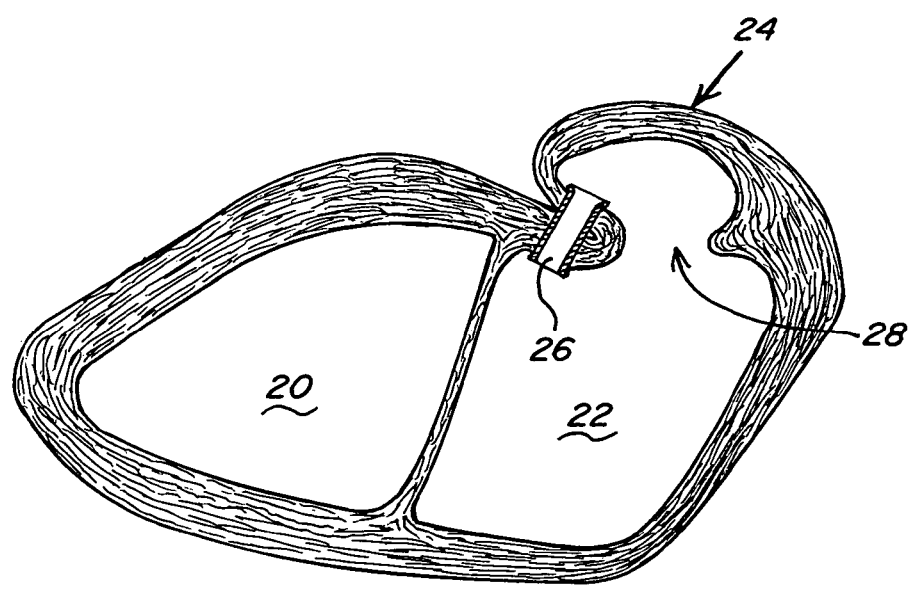
FIG. 2 is a cross-sectional view of the heart showing a connector conduit between the LAA and the rest of the left atrium.

Referring to FIG. 2, the heart is shown with a right atrium 20 and left atrium 22, with the left atrium including a left atrial appendage (LAA) 24. As shown in FIG. 2, in this embodiment, a conduit 26 is provided between the LAA 24 and the main body of the left atrium 22 to allow blood to flow through the conduit 26 separate from the flow through an ostium 28 of the LAA. The idea in this case is to not restrict the flow, but to enhance blood flow between the LAA and another blood holding or carrying portion, in this case the left atrium, and thereby reduce the likelihood of stagnation and the resulting formation of clots.

Figure 3A:
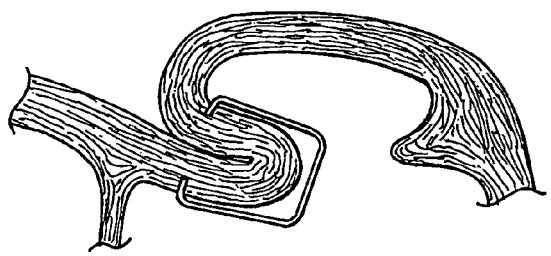
FIGS. 3A-3E are drawings showing embodiments for providing a tubular conduit within the heart.
Figure 3B:
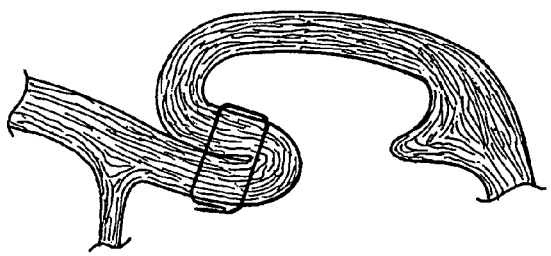
Figure 3C:
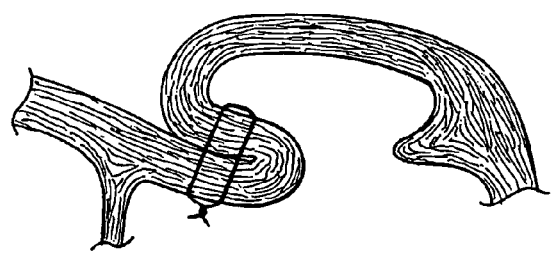
Figure 3D:
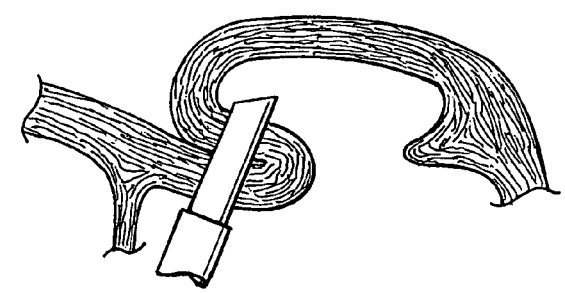
Figure 3E:
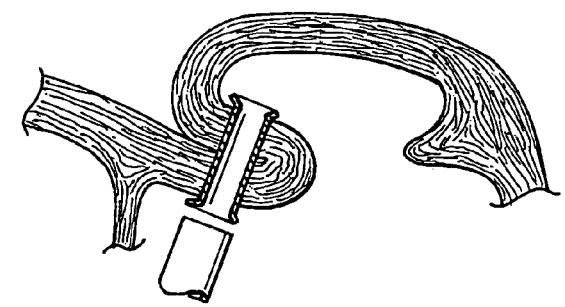

Referring to FIGS. 3A-3E, exemplary procedures include a process in which LAA 24 is constrained in a position close to the left atrial wall by means of clamping (FIG. 3A), stapling (FIG. 3B), or suturing (FIG. 3C). A puncture is then created through the walls of the LAA and LA (FIG. 3D), and the conduit is deployed through the puncture (FIG. 3E).

In this embodiment, the conduit has an outer diameter (OD) that is preferably shaped like a rivet. On delivery, the larger diameter portions at the ends may be folded down to reduce the profile of the device as it passes through a delivery catheter. Other outer diameter configurations could be used, although it is desirable to have a mechanism to hold the conduit in place. For this purpose, hooks, anchors, or struts could be included in the design of the conduit.

The inner diameter (ID) can be tubular, preferably circular, and can include a coating of anti-coagulant or anti-platelet drugs if desired.

The conduit could be made of a tubular vascular graft material, such as knitted or woven polyester, in which case nitinol anchors could be used. Another possible material for the conduit would be nitinol, but other biocompatible metals or polymers can be used. If a polymer is used, it is preferably treated to be radiopaque. The material used for the conduit could be bioresorbable. The conduit can be coated with an anti-coagulant, such as heparin. The conduit or an incision ID would preferably range from 1 to 10 mm.

A conduit is shown as being provided from the LAA to the main body of the left atrium, but a passage could be provided to other blood carrying parts of the body, such as a pulmonary vein. In each case, a blood flow path is created from a part of the body through the LAA separate from the path between the ostium of the LAA and the main body of the left atrium.

The conduit can be delivered through a catheter, such as a 5 F-12 F catheter (or possibly as high as 14 F), using generally known techniques; alternatively, it could be implanted surgically. An incision rather than a conduit could provide a path allowing blood to flow. Such an incision could also be made via a catheter or through surgery.

Having described certain embodiments, it should be apparent that modifications can be made without departing from the scope of the invention as defined by the appended claims. For example, filters could additionally be provided across the ostium and in the conduit.

What is claimed is:

1. A method of delivering a conduit to a delivery location, the method comprising inserting the conduit between a left atrial appendage (LAA) and another blood carrying portion of the body while maintaining a natural ostium of the LAA at least partially open, wherein the another blood carrying portion of the body is a main body of a left atrium, the conduit is adapted to pass blood from the LAA to the other blood carrying portion of the body, and the conduit enhances blood flow between the LAA and the left atrium, thereby reducing the likelihood of stagnation and the formation of clots.

2. A method comprising providing a conduit between a left atrial appendage (LAA) and another blood carrying portion of the body while maintaining a natural ostium of the LAA at least partially open, wherein the conduit is adapted to pass blood from the LAA to the other blood carrying portion of the body and wherein the other blood carrying portion of the body is a main body of a left atrium, the method further including constraining at least a portion of the LAA against a wall of the left atrium.

3. The method of claim 2, wherein the constraining includes clamping the LAA and a wall of the left atrium.

4. The method of claim 2, wherein the constraining includes stapling the LAA and a wall of the left atrium.

5. The method of claim 2, wherein the constraining includes suturing the LAA and a wall of the left atrium.

6. The method of claim 2, further comprising forming a puncture through the walls of the LAA and the left atrium, and deploying the conduit through the puncture.

7. The method of claim 6, wherein the conduit has an outer diameter (OD) shaped like a rivet.

8. The method of claim 6, wherein the conduit is provided through a delivery catheter.

9. The method of claim 8, wherein the conduit has larger diameter portions at its ends that can be folded down to reduce the profile of the device as it passes through the delivery catheter.

10. The method of claim 1, further comprising holding the conduit in place with hooks, anchors, and/or struts.

11. The method of claim 1, wherein an inner diameter (ID) of the conduit is circular.

12. The method of claim 1, wherein an inner diameter (ID) of the conduit includes a coating of anti-coagulant or anti-platelet drug.

13. The method of claim 1, wherein the conduit is made of a vascular graft material.

14. The method of claim 1, wherein the conduit is made of nitinol.

15. The method of claim 1, wherein the conduit is made of a bioresorbable material.

16. The method of claim 1, wherein the conduit is coated with an anti-coagulant.

17. The method of claim 1, wherein the conduit is delivered through a catheter.

18. The method of claim 1, wherein the conduit is implanted surgically.

19. A method comprising providing a conduit between a left atrial appendage (LAA) and another blood carrying portion of the body while maintaining a natural ostium of the LAA at least partially open, wherein the conduit is adapted to pass blood from the LAA to the other blood carrying portion of the body and wherein the other blood carrying portion of the body is a pulmonary vein.

* * * * *